US009034029B2

(12) United States Patent
Thompson

(10) Patent No.: US 9,034,029 B2
(45) Date of Patent: May 19, 2015

(54) STENTS WITH TAPERED STRUTS

(75) Inventor: Paul J. Thompson, New Hope, MN (US)

(73) Assignee: Covidien LP, Mansfield, MA (US)

( * ) Notice: Subject to any disclaimer, the term of this patent is extended or adjusted under 35 U.S.C. 154(b) by 331 days.

(21) Appl. No.: 12/611,114

(22) Filed: Nov. 2, 2009

(65) Prior Publication Data
US 2010/0228338 A1 Sep. 9, 2010

Related U.S. Application Data

(63) Continuation of application No. 11/533,591, filed on Sep. 20, 2006, now abandoned, which is a continuation of application No. 10/389,273, filed on Mar. 12, 2003, now abandoned, which is a continuation of application No. 09/765,725, filed on Jan. 18, 2001, now Pat. No. 6,558,415, which is a continuation-in-part of application No. 09/545,810, filed on Apr. 7, 2000, now Pat. No. 6,358,274, which is a continuation of application No. 09/049,486, filed on Mar. 27, 1998, now Pat. No. 6,132,460.

(51) Int. Cl.
*A61F 2/89* (2013.01)
*A61F 2/915* (2013.01)

(52) U.S. Cl.
CPC ....... *A61F 2/915* (2013.01); *A61F 2002/91575* (2013.01); *A61F 2002/9155* (2013.01); *A61F 2/89* (2013.01); *A61F 2210/0014* (2013.01); *A61F 2002/91508* (2013.01); *A61F 2002/91541* (2013.01); *A61F 2002/91558* (2013.01); *A61F 2250/0036* (2013.01); *A61F 2230/0013* (2013.01); *A61F 2230/0054* (2013.01)

(58) Field of Classification Search
CPC ................ A61F 2250/0036; A61F 2250/0039; A61F 2250/0014; A61F 2210/0014; A61F 2002/91575; A61F 2002/9155; A61F 2/915
USPC ....................................... 623/1.15
See application file for complete search history.

(56) References Cited

U.S. PATENT DOCUMENTS 4,733,665 A 3/1988 Palmaz
4,739,762 A 4/1988 Palmaz
(Continued)

FOREIGN PATENT DOCUMENTS

DE 197 22 384 A1 12/1998
EP 0 709 067 A2 5/1996
(Continued)

OTHER PUBLICATIONS

Extended European Search Report corresponding to European Application No. EP 10 18 6231.6, completed Aug. 22, 2011 and mailed Sep. 1, 2011; 9 pages.
(Continued)

*Primary Examiner* — Thomas J Sweet
*Assistant Examiner* — Cheryl Miller
(74) *Attorney, Agent, or Firm* — Alana T. Bergman, Esq.

(57) ABSTRACT

A stent may include a stent body having a stent axis. The stent body may include structural members defining openings through the stent body. The structural members are provided with regions having different widths. The relative sizes of the widths are selected to control the length of the stent body as the stent body is radially expanded from an undeployed orientation to a deployed orientation. In one embodiment, the regions having different widths are provided by tapering the widths of selected segments of the structural member.

15 Claims, 10 Drawing Sheets

(56) References Cited

U.S. PATENT DOCUMENTS

| | | | |
|---|---|---|---|
| 4,768,507 A | 9/1988 | Fischell et al. | |
| 4,776,337 A | 10/1988 | Palmaz | |
| 4,913,141 A | 4/1990 | Hillstead | |
| 5,019,085 A | 5/1991 | Hillstead | |
| 5,026,377 A | 6/1991 | Burton et al. | |
| 5,195,984 A | 3/1993 | Schatz | |
| 5,342,348 A | 8/1994 | Kaplan | |
| 5,419,760 A | 5/1995 | Narciso, Jr. | |
| 5,421,955 A | 6/1995 | Lau et al. | |
| 5,443,500 A | 8/1995 | Sigwart | |
| 5,449,373 A | 9/1995 | Pinchasik et al. | |
| 5,476,508 A | 12/1995 | Amstrup | |
| 5,514,154 A | 5/1996 | Lau et al. | |
| 5,540,712 A | 7/1996 | Kleshinski et al. | |
| 5,569,295 A | 10/1996 | Lam | |
| 5,591,172 A | 1/1997 | Bachmann et al. | |
| 5,591,197 A | 1/1997 | Orth et al. | |
| 5,649,977 A | 7/1997 | Campbell | |
| 5,695,499 A | 12/1997 | Helgerson et al. | |
| 5,695,516 A | 12/1997 | Fischell et al. | |
| 5,697,971 A | 12/1997 | Fischell et al. | |
| 5,707,386 A | 1/1998 | Schnepp-Pesch et al. | |
| 5,707,387 A | 1/1998 | Wijay | |
| 5,718,713 A | 2/1998 | Frantzen | |
| 5,725,572 A | 3/1998 | Lam et al. | |
| 5,728,131 A | 3/1998 | Frantzen et al. | |
| 5,741,327 A | 4/1998 | Frantzen | |
| 5,759,186 A | 6/1998 | Bachmann et al. | |
| 5,800,526 A | 9/1998 | Anderson et al. | |
| 5,807,404 A | 9/1998 | Richter | |
| 5,810,872 A | 9/1998 | Kanesaka et al. | |
| 5,817,102 A | 10/1998 | Johnson et al. | |
| 5,843,117 A | 12/1998 | Alt et al. | |
| 5,853,419 A | 12/1998 | Imran | |
| 5,855,600 A | 1/1999 | Alt | |
| 5,861,027 A * | 1/1999 | Trapp | 623/1.15 |
| 5,888,201 A | 3/1999 | Stinson et al. | |
| 5,895,406 A * | 4/1999 | Gray et al. | 623/1.15 |
| 5,928,280 A | 7/1999 | Hansen et al. | |
| 5,931,867 A * | 8/1999 | Haindl | 623/1.15 |
| 5,954,729 A | 9/1999 | Bachmann et al. | |
| 6,042,606 A | 3/2000 | Frantzen | |
| 6,077,295 A | 6/2000 | Limon et al. | |
| 6,083,259 A | 7/2000 | Frantzen | |
| 6,120,522 A | 9/2000 | Vrba et al. | |
| 6,132,460 A | 10/2000 | Thompson | |
| 6,132,461 A | 10/2000 | Thompson | |
| 6,190,406 B1 * | 2/2001 | Duerig et al. | 623/1.2 |
| 6,203,569 B1 | 3/2001 | Wijay | |
| 6,206,910 B1 * | 3/2001 | Berry et al. | 623/1.15 |
| 6,231,598 B1 | 5/2001 | Berry et al. | |
| 6,273,911 B1 | 8/2001 | Cox et al. | |
| 6,287,336 B1 | 9/2001 | Globerman et al. | |
| 6,299,635 B1 | 10/2001 | Frantzen | |
| 6,309,414 B1 | 10/2001 | Rolando | |
| 6,312,459 B1 | 11/2001 | Huang | |
| 6,325,825 B1 | 12/2001 | Kula et al. | |
| 6,423,090 B1 * | 7/2002 | Hancock | 623/1.15 |
| 6,471,720 B1 * | 10/2002 | Ehr et al. | 623/1.15 |
| 6,485,509 B2 * | 11/2002 | Killion et al. | 623/1.15 |
| 6,491,718 B1 * | 12/2002 | Ahmad | 623/1.15 |
| 6,540,774 B1 * | 4/2003 | Cox | 623/1.15 |
| 6,547,818 B1 * | 4/2003 | Rourke et al. | 623/1.15 |
| 6,558,415 B2 * | 5/2003 | Thompson | 623/1.16 |
| 6,626,935 B1 * | 9/2003 | Ainsworth et al. | 623/1.15 |
| 6,764,507 B2 * | 7/2004 | Shanley et al. | 623/1.16 |
| 2001/0016770 A1 | 8/2001 | Allen et al. | |
| 2001/0044649 A1 * | 11/2001 | Vallana et al. | 623/1.15 |
| 2002/0049490 A1 * | 4/2002 | Pollock et al. | 623/1.15 |

FOREIGN PATENT DOCUMENTS

| | | |
|---|---|---|
| EP | 0 732 088 A2 | 9/1996 |
| EP | 0 800 800 A1 | 10/1997 |
| EP | 0 830 853 A1 | 3/1998 |
| EP | 0 997 115 A2 | 5/2000 |
| FR | 2 764 794 A1 | 12/1998 |
| WO | WO 99/21509 A1 | 5/1999 |
| WO | WO 99/39660 A1 | 8/1999 |
| WO | WO 99/49810 A1 | 10/1999 |

OTHER PUBLICATIONS

Extended European Search Report corresponding to European Application No. EP 10 18 6236.5, completed Aug. 22, 2011 and mailed Sep. 6, 2011; 9 pages.

* cited by examiner

STENTS WITH TAPERED STRUTS

CROSS-REFERENCE TO RELATED APPLICATIONS

This application is a continuation of co-pending and commonly assigned U.S. patent application Ser. No. 11/533,591 filed Sep. 20, 2006, which is a continuation of U.S. patent application Ser. No. 10/389,273 filed Mar. 12, 2003, now abandoned, which is a continuation of U.S. patent application Ser. No. 09/765,725 filed Jan. 18, 2001, now U.S. Pat. No. 6,558,415, which is a continuation-in-part of U.S. patent application Ser. No. 09/545,810 filed Apr. 7, 2000, now U.S. Pat. No. 6,358,274, which is a continuation of U.S. patent application Ser. No. 09/049,486 filed Mar. 27, 1998, now U.S. Pat. No. 6,132,460, all of which are incorporated herein by reference in their entirety.

TECHNICAL FIELD

The present disclosure pertains to stents for use in intraluminal applications. More particularly, this disclosure pertains to a novel structure for such stents.

BACKGROUND

Stents are widely used for numerous applications where the stent is placed in the lumen of a patient and expanded. Such stents may be used in coronary or other vasculature, as well as other body lumens.

Commonly, stents are cylindrical members. The stents expand from reduced diameters to enlarged diameters. Frequently, such stents are placed on a balloon catheter with the stent in the reduced-diameter state. So placed, the stent is advanced on the catheter to a placement site. At the site, the balloon is inflated to expand the stent to the enlarged diameter. The balloon is deflated and removed, leaving the enlarged diameter stent in place. So used, such stents are used to expand occluded sites within a patient's vasculature or other lumen.

Examples of prior art stents are numerous. For example, U.S. Pat. No. 5,449,373 to Pinchasik et al. teaches a stent with at least two rigid segments joined by a flexible connector. U.S. Pat. No. 5,695,516 to Fischell teaches a stent with a cell having a butterfly shape when the stent is in a reduced-diameter state. Upon expansion of the stent, the cell assumes a hexagonal shape.

In stent design, it is desirable for the stent to be flexible along its longitudinal axis to permit passage of the stent through arcuate segments of a patient's vasculature or other body lumen. Preferably, the stent will have at most minimal longitudinal shrinkage when expanded and will resist compressive forces once expanded.

SUMMARY OF INVENTION

The present disclosure relates to a stent including a stent body having a stent axis. The stent body includes structural members that define openings through the stent body. The structural members are provided with regions having different widths. The relative sizes of the widths are selected to control the length of the stent body as the stent body is radially expanded from an un-deployed orientation to a deployed orientation. In one embodiment, the regions having different widths are provided by tapering the widths of selected segments of the structural member. In a preferred embodiment, the relative sizes of the widths are selected to minimize or eliminate length changes as the stent body is expanded from the un-deployed orientation to the expanded orientation.

DETAILED DESCRIPTION

Referring now to the several drawing figures in which identical elements are numbered identically, a description of the preferred embodiment of the present invention will now be provided. Where several embodiments are shown, common elements are similarly numbered and not separately described with the addition of apostrophes to distinguish the embodiments.

Figure 1:
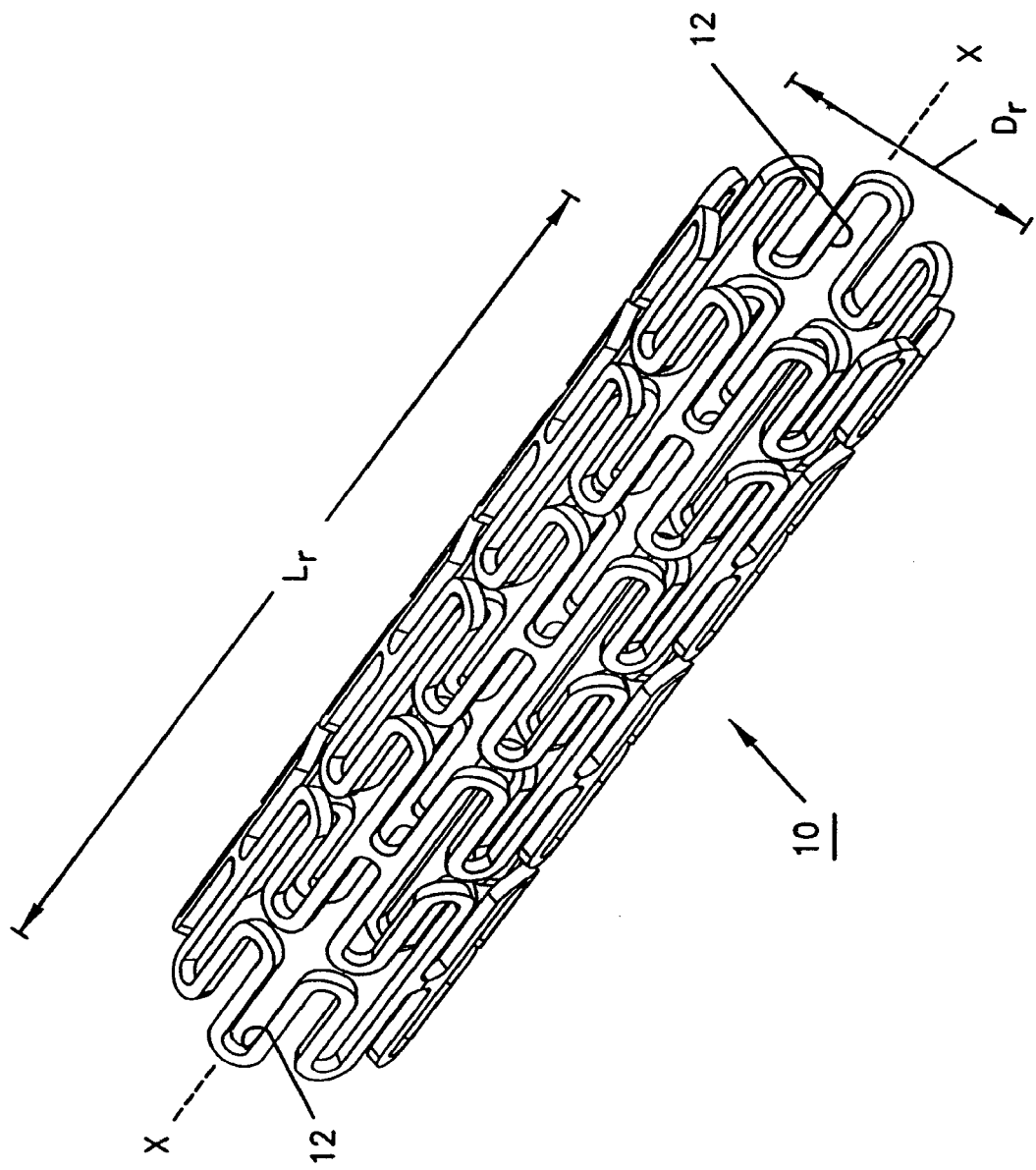
FIG. 1 is a perspective view of a first embodiment of a stent according to the present invention shown in a rest diameter state and showing a plurality of stent cells each having a major axis perpendicular to an axis of the stent.
Figure 2:
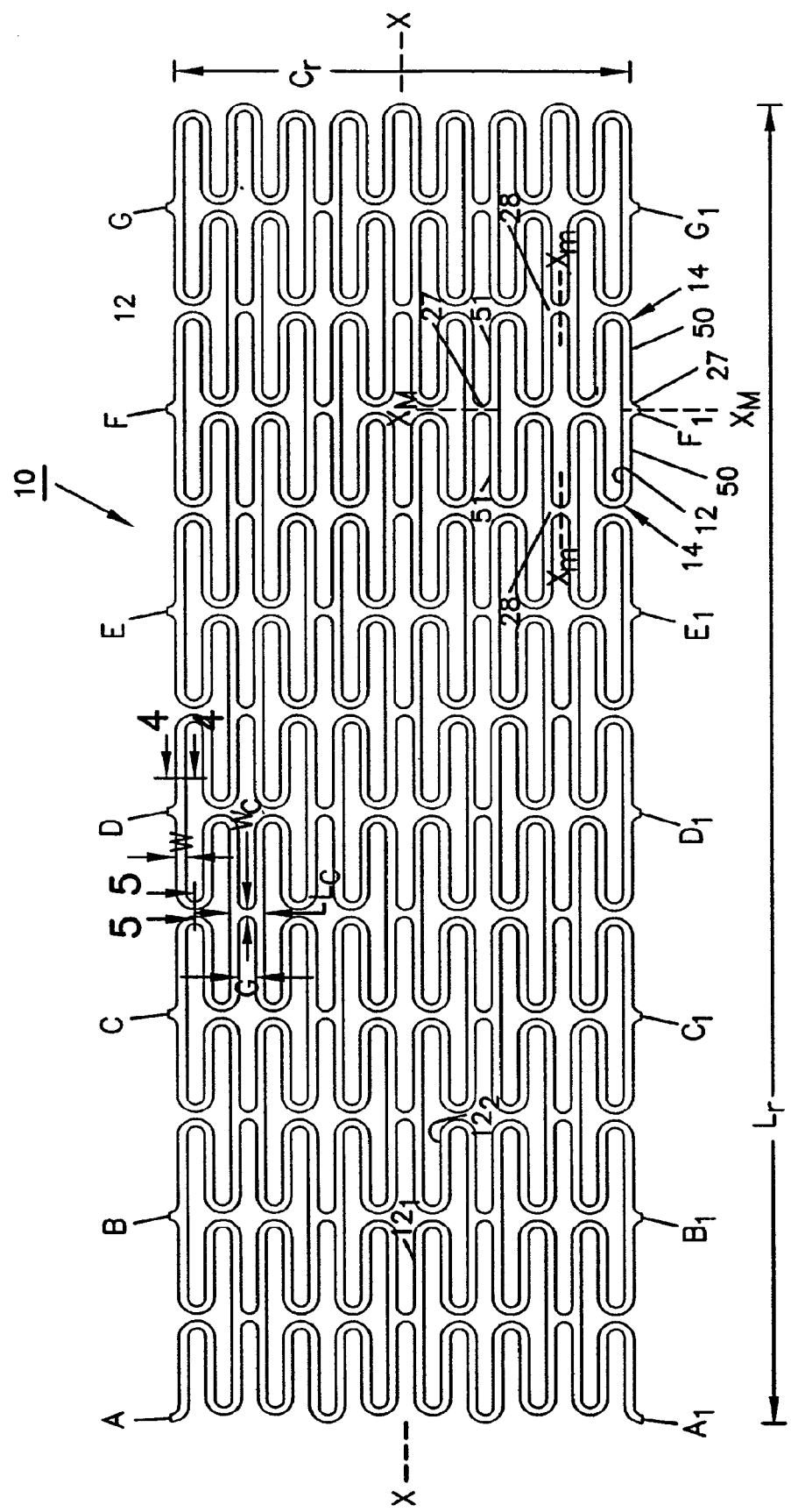
FIG. 2 is a plan view of the stent of FIG. 1 as it would appear if it were longitudinally split and laid out flat.
Figure 6:
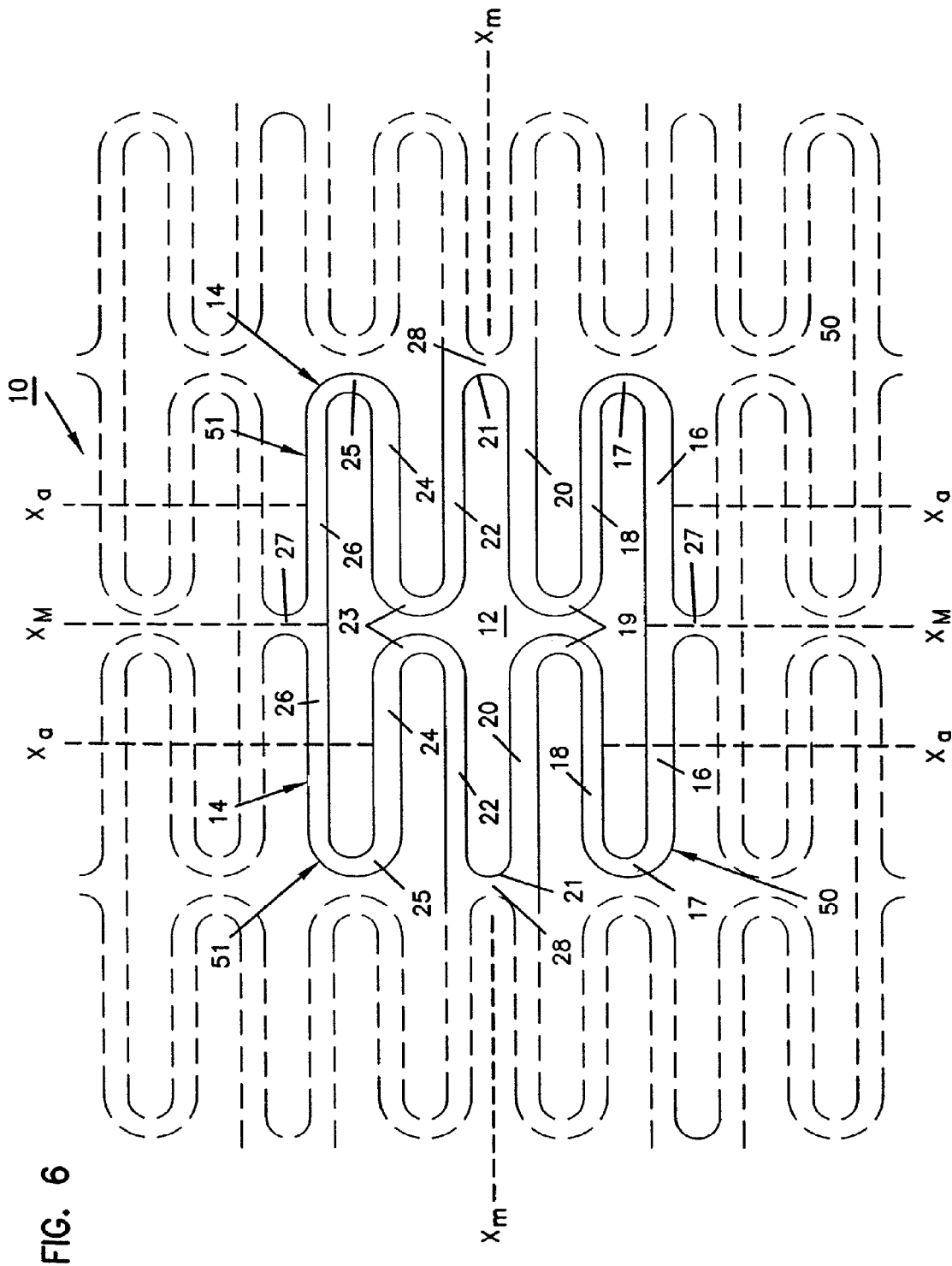
FIG. 6 is an enlarged view of a portion of FIG. 2 illustrating a cell structure with material of the stent surrounding adjacent cells shown in phantom lines.

FIG. 1 illustrates a stent 10 having a rest length $L_r$ and an un-deployed or reduced diameter $D_r$. For ease of illustration, the stent 10 is shown flat in FIG. 2 which illustrates a rest circumference $C_r$ ($C_r = \pi D_r$). In FIG. 2, locations A, B, C, D, E, F and G are shown severed from their normally integrally formed locations $A_1$, $B_1$, $C_1$, $D_1$, $E_1$, $F_1$, and $G_1$. This permits the stent 10 to be shown as if it were severed at normally integrally formed locations A-$A_1$, B-$B_1$, C-$C_1$, D-$D_1$, E-$E_1$, F-$F_1$, and G-$G_1$ and laid flat. FIG. 6 is an enlarged portion of the view of FIG. 2 to better illustrate a novel cell structure as will be described.

Figure 3:
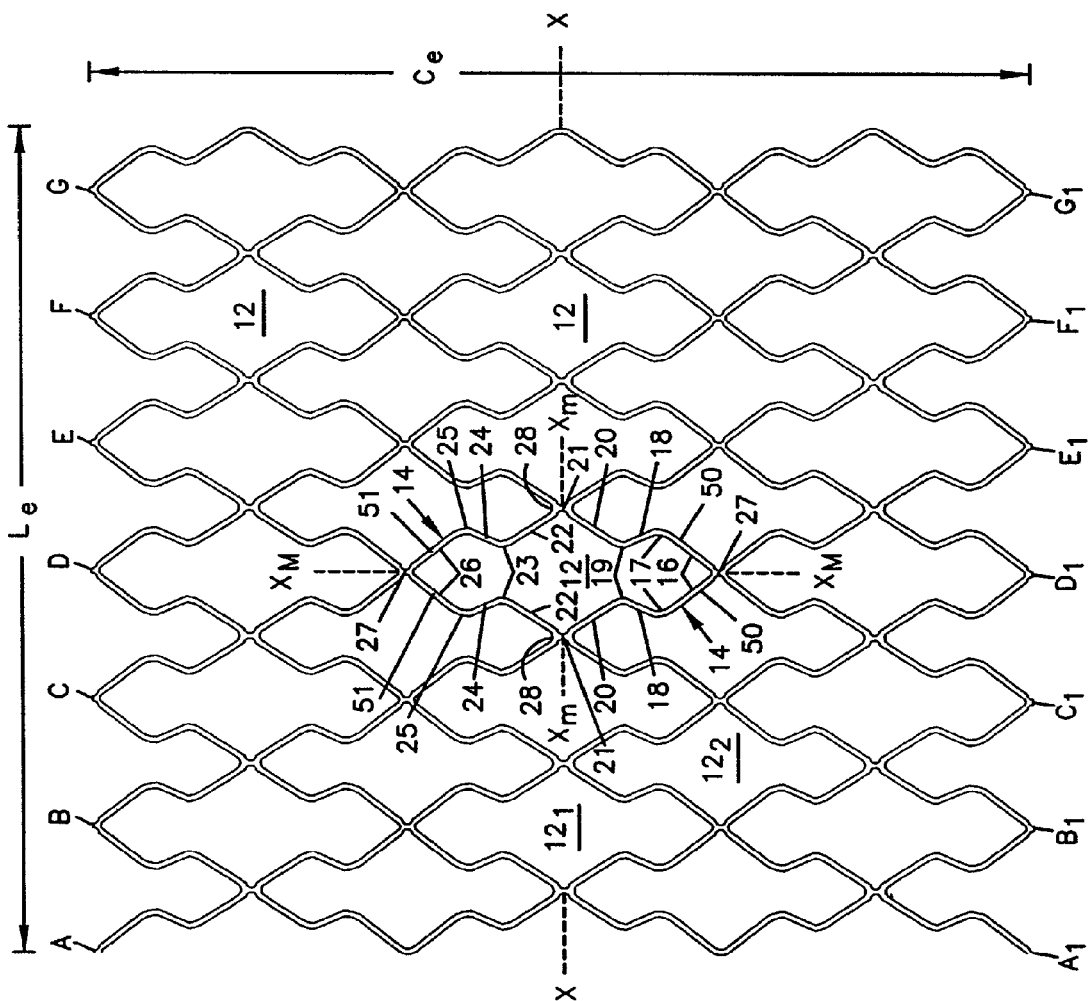
FIG. 3 is the view of FIG. 2 following expansion of the stent to an enlarged diameter.

The stent 10 is a reticulated, hollow tube. The stent 10 may be expanded from the rest diameter $D_r$ (and corresponding rest circumference $C_r$) to an expanded or enlarged diameter. FIG. 3 is a view similar to FIG. 2 (i.e., illustrating the expanded stent 10 as it would appear if longitudinally split and laid flat). Since FIG. 3 is a two-dimensional representation, the enlarged diameter is not shown. However, the enlarged circumference $C_e$ is shown as well as a length $L_e$ following expansion. The expanded diameter is equal to $C_e/\pi$.

As will be discussed length $L_e$ is preferably not more than minimally smaller (e.g., less than 10% smaller) than length $L_r$. Ideally, $L_e$ equals $L_r$.

The material of the stent 10 defines a plurality of cells 12. The cells 12 are bounded areas which are open (i.e., extend through the wall thickness of the stent 10). The stent 10 may be formed through any suitable means including laser or chemical milling. In such processes, a hollow cylindrical tube is milled to remove material and form the open cells 12.

Figure 8:
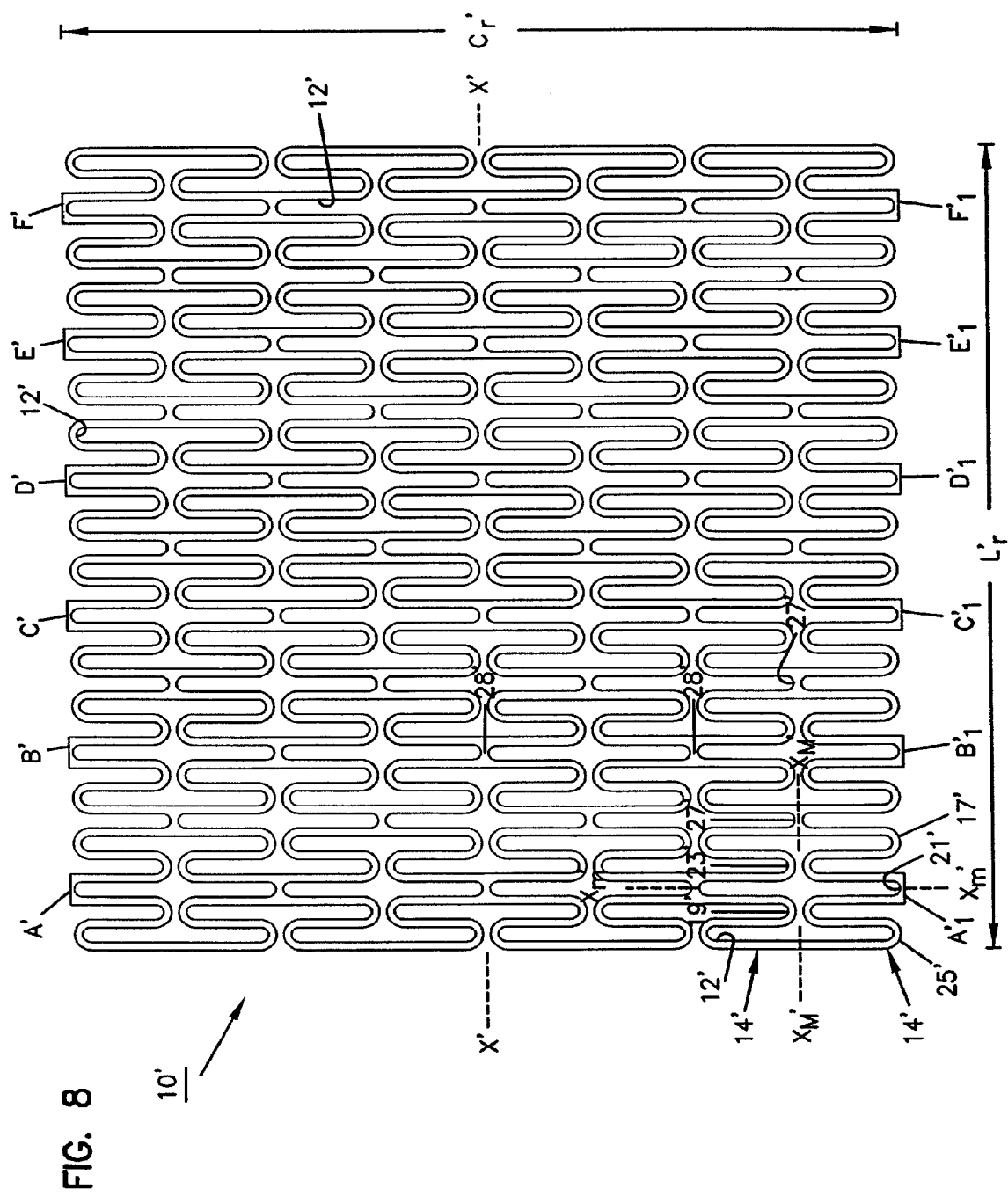
FIG. 8 is the view of FIG. 2 showing an alternative embodiment of the present invention with a major axis of the cell being parallel to an axis of the stent.
Figure 9:
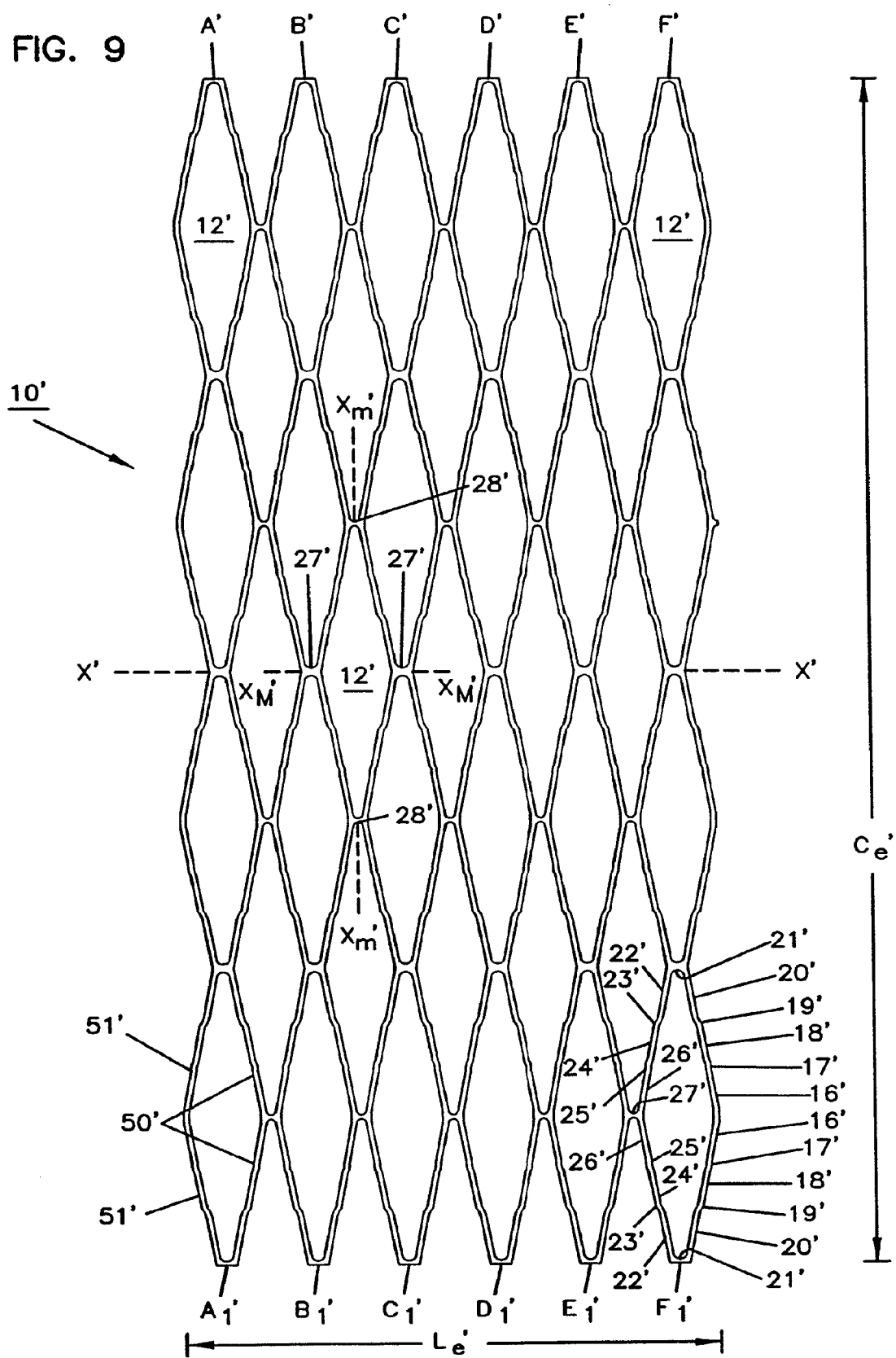
FIG. 9 is the view of FIG. 8 following expansion of the stent to an enlarged diameter.

The cells 12 have a longitudinal or major axis $X_M$-$X_M$ and a transverse or minor axis $X_m$-$X_m$. In the embodiments of FIGS. 1-3, the major axis $X_M$-$X_M$ is perpendicular to the longitudinal cylindrical axis X-X of the stent 10. In the embodiments of FIGS. 8 and 9, the major axis $X_M'$-$X_M'$ is parallel to the longitudinal cylindrical axis X'-X' of the stent 10'. The cell 12 is symmetrical about axes $X_M$-$X_M$ and $X_m$-$X_m$.

The cell 12 is defined by portions of the tube material including first and second longitudinal segments 14. The segments 14 each have a longitudinal axis $X_a$-$X_a$ as shown in FIG. 6. The segments' longitudinal axes $X_a$-$X_a$ are parallel to and positioned on opposite sides of the cell major axis $X_M$-$X_M$.

Each of longitudinal segments 14 has an undulating pattern to define a plurality of peaks 17, 21, 25 and valleys 19, 23. The peaks 17, 21, 25 are spaced outwardly from the longitudinal axes $X_a$-$X_a$ and the valleys 19, 23 are spaced inwardly from the longitudinal axes $X_a$-$X_a$. As used in this context, "inward" and "outward" mean toward and away from, respectively, the cell's major axis $X_M$-$X_M$.

Each of the peaks 17, 21, 25 and valleys 19, 23 is a generally semi-circular arcuate segment. The peaks 17, 21, 25 and valleys 19, 23 are joined by parallel and spaced-apart straight segments 16, 18, 20, 22, 24 and 26 which extend perpendicular to the major axis $X_M$-$X_M$. Linearly aligned straight end portions 16, 26 of opposing segments 14 are joined at first and second longitudinal connection locations 27 spaced apart on the major axis $X_M$-$X_M$. First and second transverse connection locations 28 are spaced apart on the minor axis $X_m$-$X_m$. The first and second transverse connection locations 28 are positioned at the apices of the center peaks 21 of the longitudinal segments 14.

Figure 4:
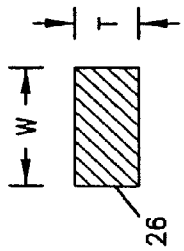
FIG. 4 is a view taken along line 4-4 in FIG. 2.

Except as will be described, the segments 14 have uniform cross-sectional dimensions throughout their length as illustrated in FIG. 4. By way of non-limiting example, the width W and thickness T of the straight line segments 16, 18, 20, 22, 24 and 26 are about 0.0065 inch (about 0.16 mm) and about 0.0057 inch (about 0.14 mm), respectively.

Figure 5:
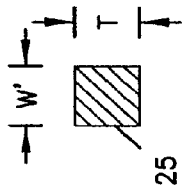
FIG. 5 is a view taken along line 5-5 in FIG. 2.

For reasons that will be described, the width W' (FIG. 5) at the apices of the peaks 17, 21, 25 and valleys 19, 23 is narrower than width W (in the example given, narrow width W' is about 0.0055 inch or about 0.13 mm). The width of the peaks 17, 21, 25 and valleys 19, 23 gradually increases from width W' at the apices to width W at the straight segments 16, 18, 20, 22, 24, and 26. At the longitudinal and transverse connection locations 27, 28, the width $W_C$ (shown in FIG. 2) is preferably equal to or less than the common width W.

The combined lengths of segments 16-20 to the apex of peak 21 represent a path length 50 from longitudinal connection location 27 to transverse connection location 28. Similarly the combined lengths of the other arcuate and straight segments 22-26 to the apex of peak 21 represent identical length path lengths 51 of identical geometry from longitudinal connection locations 27 to transverse connection locations 28. Each of the path lengths 50, 51 is longer than a straight-line distance between the transverse and longitudinal connection locations 27, 28. As will be described, the straight-line distance between the transverse and longitudinal connection locations 27, 28 increases as the diameter of the stent 10 is expanded. The path lengths 50, 51 are sized to be not less than the expanded straight-line distance.

The stent 10 includes a plurality of identical cells 12. Opposite edges of the segments 14 define obliquely adjacent cells (such as cells $12_1$, $12_2$ in FIG. 2). Cells 12 having major axes $X_M$-$X_M$ collinear with the major axis $X_M$-$X_M$ of cell 12 are interconnected at the longitudinal connection locations 27. Cells having minor axes collinear with the minor axis $X_m$-$X_m$ of cell 12 are interconnected at the transverse connection locations 28.

As mentioned, the stent 10 in the reduced diameter of FIG. 1 is advanced to a site in a lumen. The stent 10 is then expanded at the site. The stent 10 may be expanded through any conventional means. For example, the stent 10 in the reduced diameter may be placed on the balloon tip of a catheter. At the site, the balloon is expanded to generate radial forces on the interior of the stent 10. The radial forces urge the stent 10 to radially expand without appreciable longitudinal expansion or contraction. Plastic deformation of the material of the stent 10 (e.g., stainless steel) results in the stent 10 retaining the expanded shape following subsequent deflation of the balloon. Alternatively, the stent 10 may be formed of a super-elastic or shape memory material (such as nitinol—a well-known stent material which is an alloy of nickel and titanium).

As the stent 10 expands, the path lengths 50, 51 straighten to accommodate the expansion. FIG. 3 illustrates the straightening of the path lengths 50, 51. In FIG. 3, the stent 10 has been only partially expanded to an expanded diameter less than a maximum expanded diameter. At a maximum expanded size, the path lengths 50, 51 are fully straight. Further expansion of the stent 10 beyond the maximum expanded size would result in narrowing of the minor axis $X_m$-$X_m$ (i.e., a narrowing of a separation between the transverse connection locations and a resulting narrowing of the length $L_r$ of the stent) or would require stretching and thinning of the stent material.

As shown in FIG. 3, during expansion of the stent 10, the straight segments 16, 18, 20, 22, 24 and 26 are substantially unchanged. The straightening of the path lengths 50, 51 results in bending of the arcuate peaks 17, 21, 25 and valleys 19, 23. Since the width W' of the peaks 17, 21, 25 and valleys 19, 23 is less than the width W of the straight segments 16, 18, 20, 22, 24 and 26, the arcuate peaks 17, 21, 25 and valleys 19, 23 are less stiff than the straight segments 16, 18, 20, 22, 24 and 26 and, therefore, more likely to deform during expansion.

As the stent 10 expands, the cells 12 assume a diamond shape shown in FIG. 3. Since the expansion forces are radial, the length of the major axis $X_M$-$X_M$ (i.e., the distance between the longitudinal connection locations 27) increases. The length of the minor axis $X_m$-$X_m$ (and hence the length of the stent 10) remains unchanged.

The stent 10 is highly flexible. To advance to a site, the axis X-X of the stent 10 must bend to navigate through a curved lumen. Further, for placement at a curved site in a lumen, the stent 10 must be sufficiently flexible to retain a curved shape following expansion and to bend as the lumen bends over time. The stent 10, as described above, achieves these objections.

When bending on its axis X-X, the stent 10 tends to axially compress on the inside of the bend and axially expand on the outside of the bend. The present design permits such axial expansion and contraction. The novel cell geometry 12 results in an accordion-like structure which is highly flexible before and after radial expansion. Further, the diamond shape of the cells 12 after radial expansion resists constricting forces otherwise tending to collapse the stent 10.

Numerous modifications are possible. For example the stent 10 may be lined with either an inner or outer sleeve (such as polyester fabric or ePTFE) for tissue growth. Also, the stent may be coated with radiopaque coatings such as platinum, gold, tungsten or tantalum. In addition to materials previously discussed, the stent may be formed of any one of a wide variety of previous known materials including, without limitation, MP35N, tantalum, platinum, gold, Elgiloy and Phynox.

Figure 7:
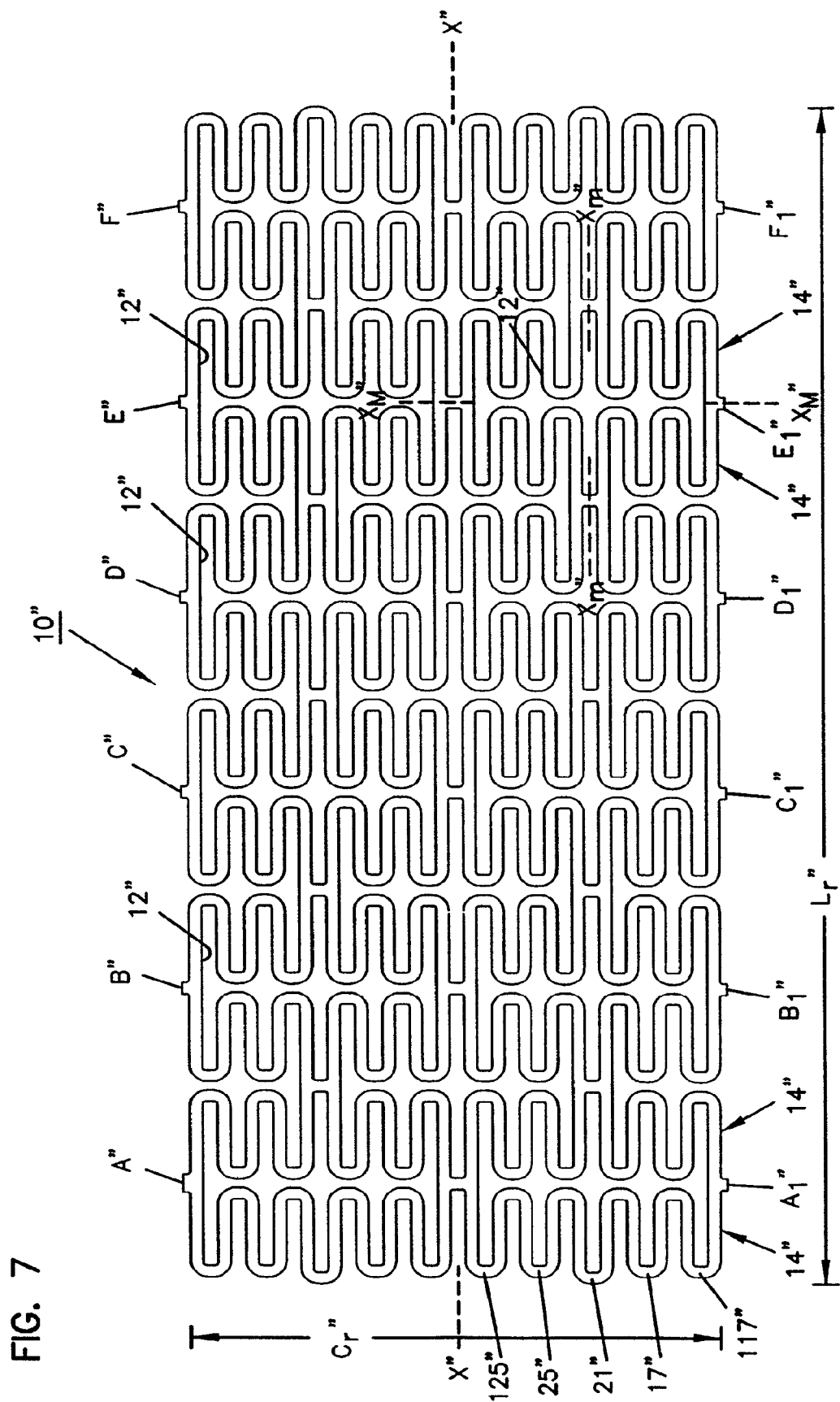
FIG. 7 is the view of FIG. 2 showing an alternative embodiment of the present invention with a cell having five peaks per longitudinal segment.

While three cells 12 are shown in FIG. 2 longitudinally connected surrounding the circumference $C_r$ of the stent, a different number could be so connected to vary the properties of the stent 10 as a designer may elect. Likewise, while each column of cells 12 in FIG. 2 is shown as having three longitudinally connected cells 12, the number of longitudinally connected cells 12 could vary to adjust the properties of the stent. Also, while each longitudinal segment 14 is shown as having three peaks 17, 21, 25 per longitudinal segment 14, the number of peaks could vary. FIG. 7 illustrates a stent 10" with a cell 12" having five peaks 117", 17", 21", 25" and 125" per longitudinal segment 14". Preferably, the longitudinal segment will have an odd number of peaks so that the transverse connection points are at an apex of a center peak.

FIGS. 8 and 9 illustrate an alternative embodiment where the major axis $X_M'$-$X_M'$ of the cells 12' are parallel with the cylindrical axis X'-X' of the stent 10'. In FIG. 9, the expanded stent 10' is shown at a near fully expanded state where the path lengths 50', 51' are substantially linear.

When forming the stent from shape memory metal such as nitinol, the stent can be laser cut from a nitinol tube. Thereafter, the stent can be subjected to a shape-setting process in which the cut tube is expanded on a mandrel and then heated. Multiple expansion and heating cycles can be used to shape-set the stent to the final expanded diameter. Preferably, the final expanded diameter is equal to the desired deployed diameter of the stent. During expansion, the stent is preferably axially restrained such that the length of the stent does not change during expansion. The finished stent preferably has an austenite finish temperature less than body temperature. Thus, at body temperature, the stent will self-expand to the desired deployed diameter due to the shape memory characteristic of the metal forming the stent.

In use, the finished stent can be mounted on a delivery catheter. As is conventionally known in the art, the stent can be held in a compressed orientation on the delivery catheter by a retractable sheath. As is also known in the art, the delivery catheter can be used to advance the stent to a deployment location (e.g., a constricted region of a vessel). At the deployment cite, the sheath is retracted thereby releasing the stent. Once released, the stent self-expands to the deployed diameter.

It has been noted that the lengths of prior art stents when mounted on a delivery catheter can be different from the deployed lengths of such stents. For example, it has been determined that the deployed lengths of the prior art stents are often shorter than the compressed orientation lengths (i.e., the lengths of the stents when mounted on a delivery catheter). Shortening can be problematic because shortening makes it more difficult for a physician to accurately place a stent at a desired position in a vessel.

An important aspect of the present invention relates to a stent design that reduces or eliminates shortening of a stent. For example, one embodiment of the present invention relates to a stent having the same length or substantially the same length at each of the following stages: 1) when the stent is initially cut from a tube of shape-memory alloy; 2) when the stent is shape-set to the desired expanded diameter; 3) when the stent is compressed on the delivery catheter; and 4) when the stent is deployed at a deployment location.

With respect to shape memory stents, it has been found that varying the width of the segments 16, 18, 20, 22, 24 and 26 controls whether the stent shortens, lengthens, or remains the same length during expansion from the compressed orientation (i.e., the reduced diameter orientation) to the deployed orientation. For example, the segments 26 and 16 are preferably constructed with enlarged widths adjacent the connection locations 27, and reduced widths adjacent their corresponding peaks 25 and 17. Similarly, the segments 22 and 20 are preferably constructed with enlarged widths adjacent the connection locations 28, and reduced widths adjacent their corresponding valleys 23 and 19. The relative sizes between the enlarged widths and the reduced widths controls whether the stent shortens, lengthens, or remains the same during expansion.

Figure 10:
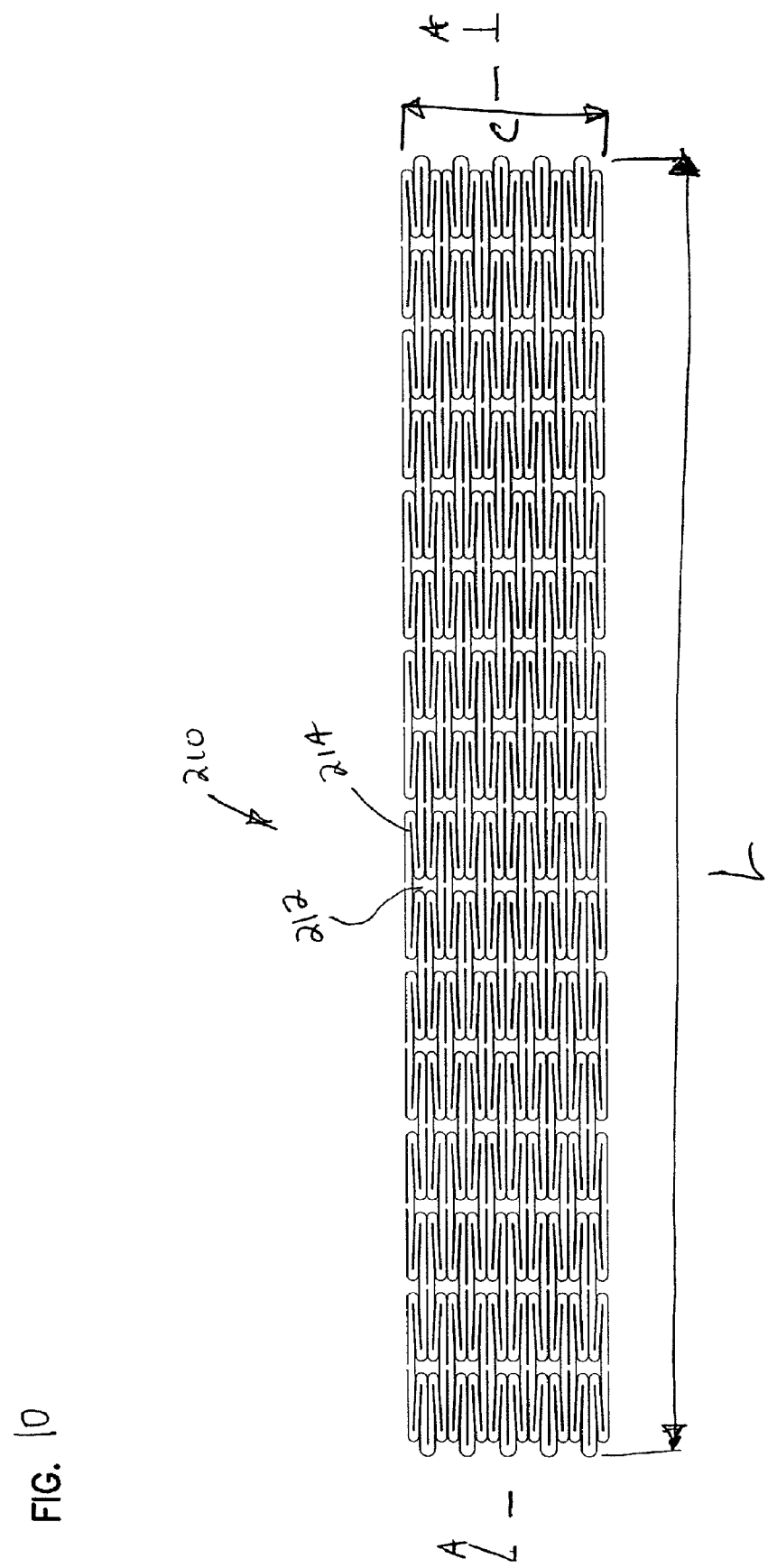
FIG. 10 is a plan view of another stent as it would appear if it were longitudinally split and laid out flat.
Figure 11:
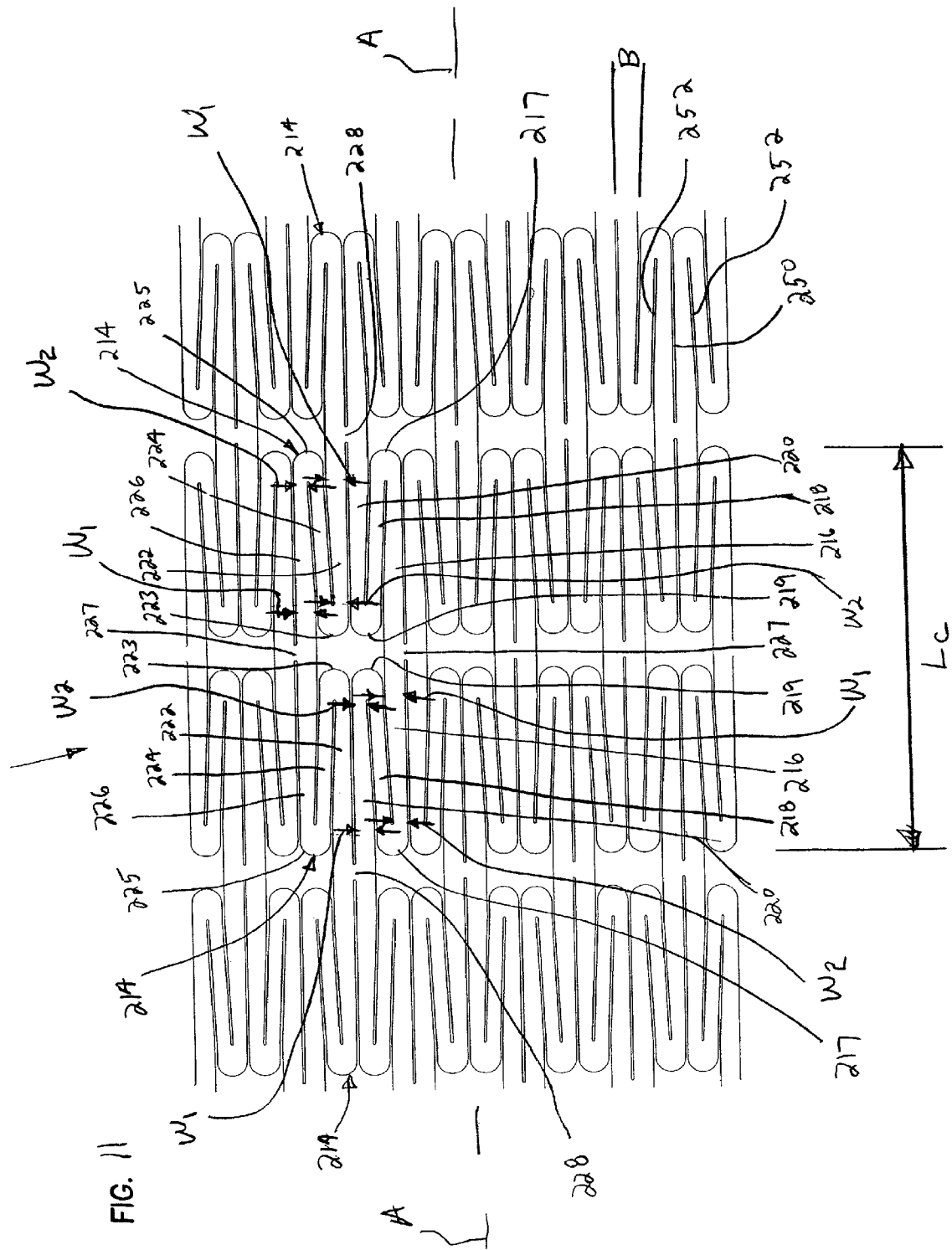
FIG. 11 is an enlarged view of a portion of the stent of FIG. 10.
Figure 12:
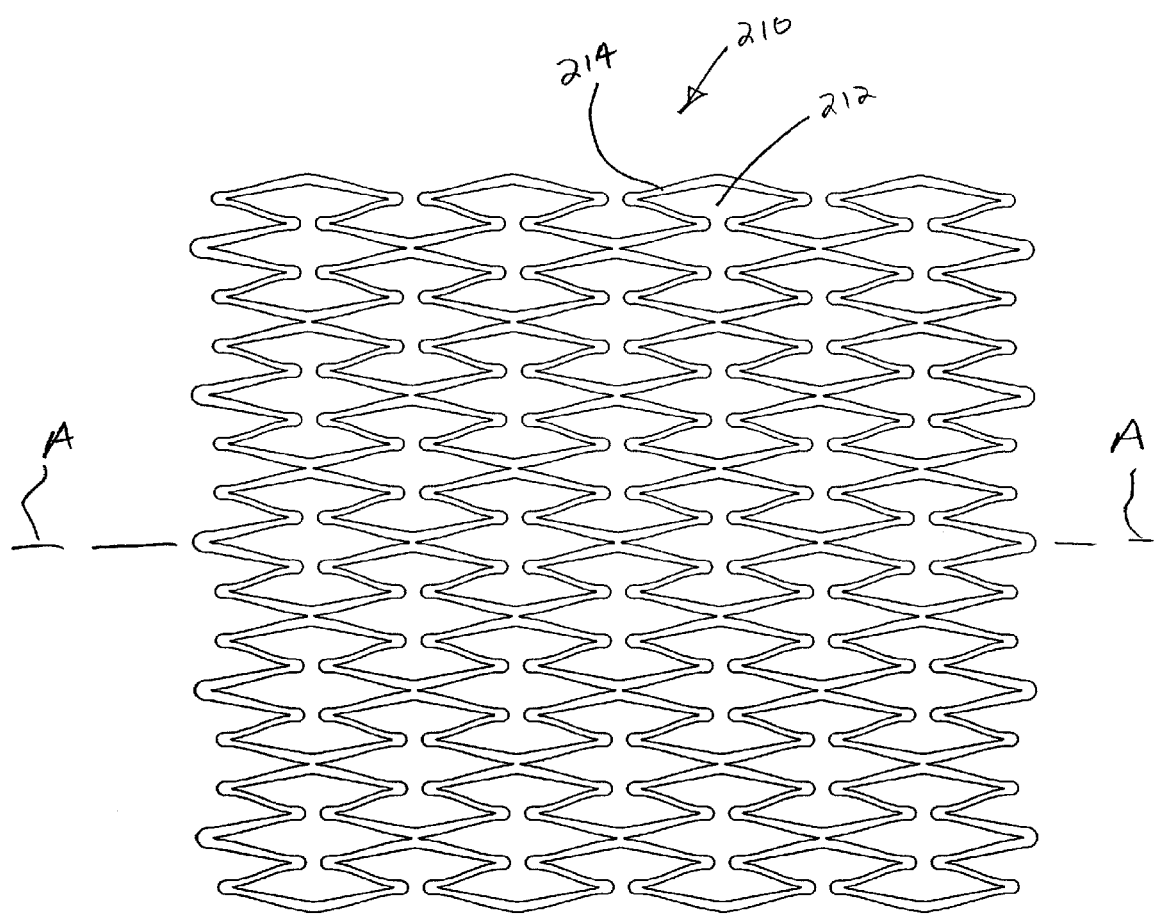
FIG. 12 is a plan view of a portion of the stent of FIG. 10 in a deployed/expanded orientation, the stent has been longitudinally cut and laid flat.

FIGS. 10-12 show a stent 210 having a cell structure adapted to limit any length changes that may occur as the stent is expanded from the compressed orientation to the deployed orientation. Preferably the length change between the compressed orientation and the deployed orientation is less than 5 percent. More preferably, the length change between the compressed orientation and the deployed orientation is less than 2 percent. Most preferably, the stent 210 experiences substantially no length change as it is released from a delivery catheter and expanded from the compressed orientation to the deployed orientation.

FIG. 10 shows the stent 210 cut longitudinally along its length and laid flat. The stent 210 has a length L and a circumference C. FIG. 10 is representative of the stent 210 after the stent 210 has been laser cut from a shape-memory tube, but before the stent 210 has been shape-set to the expanded diameter. FIG. 12 shows a portion of the stent 210 after the stent has be shape-set to the desired expanded diameter. In both FIGS. 10 and 12, the stent 210 is elongated along axis A-A and includes a stent body (i.e., a three-dimensional structure) having cell defining portions that define plurality of cells 212. After the stent 210 has been shape-set to the expanded diameter as shown in FIG. 12, the cells 212 are preferably more open than the cells 212 depicted in FIG. 10. However, while the circumference C increases, the length L preferably remains substantially the same at both diameters.

Referring to FIG. 11, the cell defining portions of the stent body include circumferential connection locations 227 and longitudinal connection locations 228. "Circumferential connection locations" are locations where circumferentially adjacent cell defining structures, as defined relative to axis A-A, are connected together. "Longitudinal connection locations" are locations where longitudinally adjacent cell defining portions, as define relative to the axis A-A, are connected together.

Referring still to FIG. 11, each cell defining portion includes two axially spaced-apart members 214 (i.e., members that are spaced-apart from one another along the axis A-A) that extend circumferentially about the axis A-A in an undulating pattern. The members 214 extend in the undulating pattern between the circumferential connection locations 227. Adjacent the circumferential connection locations 227, the ends of the undulating members 214 are connected to one another. At the longitudinal connection locations 228, the undulating members 214 merge with the undulating members 214 of longitudinally adjacent cell defining portions.

Still referring to FIG. 11, each undulating member 214 is shown including: 1) a segment 226 that extends from connection location 227 to peak 225; 2) a segment 224 that extends from peak 225 to valley 223; 3) a segment 222 that extends from valley 223 to connection location 228; 4) a segment 220 that extends from connection location 228 to valley 219; 5) a segment 218 that extends from valley 219 to peak 217; and 6) a segment 216 that extends from peak 217 to connection location 227. The segments 216-226 preferably extend generally longitudinally along the stent 210. The term "generally longitudinally" will be understood to mean that the segments 216-226 are closer to a parallel relationship relative to the axis A-A of the stent 210 than to a transverse relationship relative to the axis A-A of the stent 210.

To prevent length changes during deployment of the stent, the segments 226 and 216 preferably include enlarged widths $W_1$ adjacent the connection locations 227, and reduced widths $W_2$ adjacent their corresponding peaks 225 and 217. Similarly, the segments 222 and 220 are preferably constructed with enlarged widths $W_1$ adjacent the connection locations 228, and reduced widths $W_2$ adjacent their corresponding valleys 223 and 219. Preferably, widths of the segments 226, 222, 220 and 216 taper (i.e., narrow) continuously along their lengths. As is clear from FIG. 11, the widths of the segments are measured in a circumferential direction relative to the axis A-A.

Referring once again to FIG. 11, pairs of tapered segments 226 and 216 are provided at each circumferential connection location 227, and pairs of tapered segments 222 and 220 are provided at each longitudinal connection location 228. Each pair of tapered segments is defined by an inner cut 250 that is parallel to the axis A-A of the stent 210, and two outer cuts 252 that are angled relative to the axis A-A of the stent 210. Preferably, the outer cuts 252 diverge from one another as the cuts 252 extend toward their corresponding connection location 227 or 228. The angled orientation of the cuts 252 causes the segments 224 and 218 which interconnect the pairs of tapered segments 226, 216, 222 and 220 to have a non-tapered configuration. Additionally, the angled orientation of the cuts 252 causes the segments 224 and 218 to be angled (i.e., skewed) relative to the axis A-A of the stent 210.

The narrowing from width $W_1$ to $W_2$ results in a taper along the lengths of the segments 226, 222, 220 and 216. Preferably, the taper has an angle B in the range of 0.5-5 degrees relative to the axis A-A of the stent 210. More preferably, the taper angle B is in the range of 1-3 percent. It has been found that the relative sizes of $W_1$ and $W_2$ have an effect on the deployed length of the stent 210 (i.e., the length of the stent after deployment in a vessel) as compared to the compressed length of the stent 210 (i.e., the length of the stent when mounted on a delivery catheter). As a result, in the design of the stent, the widths $W_1$ and $W_2$ can be selected to effect a desired change in length including no change in length if so desired. For example, a stent having a 5 millimeter cell length $L_c$ (labeled on FIG. 11), a first width $W_1$ of 0.0065 inch and a second width $W_2$ of 0.0059 inch, has been found to lengthen about 10% during expansion from the compressed orientation to the deployed orientation. Alternatively, a stent having a 5 millimeter cell length $L_c$ (labeled on FIG. 11), a first width $W_1$ of 0.009 and a second width $W_2$ of 0.0047, has been found to shorten about 10% during expansion from the compressed orientation to the deployed orientation. Further, a stent with a 5 millimeter cell length $L_c$ (labeled on FIG. 11), a first width $W_1$ of 0.008 inches, a second width $W_2$ of 0.0052 inches and an angle B of two degrees has been found to experience no lengthening and no shortening when expanded from the compressed orientation and the deployed orientation.

While a preferred use for the inventive features disclosed in FIGS. 10-12 is in a self-expanding stent, the features also have benefits when used with non-self-expanding stents (e.g., balloon expandable stents made of a material such as stainless steel). Also, while FIGS. 10-12 illustrate a preferred geometry for practicing the present invention, the technique for controlling length variations by varying the widths of selected portions of a stent is also applicable to stents having other geometries, shapes, or strut patterns. Further, the various aspects of the present invention can also be used to cause a desired shortening or lengthening of a stent during deployment.

It will be apparent to those skilled in the art that various modifications and variations can be made to the stents of the present disclosure without departing from the scope of the invention. Other embodiments of the invention will be apparent to those skilled in the art from consideration of the specification and practice of the invention disclosed herein. It is intended that the specification and examples be considered as exemplary only.

What is claimed is:

1. A stent of comprising:
   a stent body defining a longitudinal axis, the stent body including a plurality of structural members extending in an undulating pattern about a circumference of the stent body;
   longitudinally adjacent structural members being connected to define a plurality of cells, each cell having a plurality of outer peaks and inner valleys coupled by segments that extend generally longitudinally between the outer peaks and inner valleys, at least some of the inner valleys of each cell being free from connection with adjacent inner valleys;
   each cell being connected to a circumferentially adjacent cell about a circumference of the stent body at a circumferential connection region, each circumferential connection region connecting adjacent inner valleys;
   at least one cell including a pair of first segments extending in opposed longitudinal directions from the circumferential connection region to respective first and second outer peaks, the first segments each having a width that tapers along the longitudinal axis from a first width adjacent the circumferential connection region to a second width adjacent the respective first and second outer peaks of the at least one cell, the first width being greater than the second width;
   wherein the at least one cell is connected to a longitudinally adjacent cell at a longitudinal connection region, the longitudinal connection region connecting adjacent outer peaks of the at least one cell and the longitudinally adjacent cell; and
   the at least one cell including a second segment having a width that tapers along the longitudinal axis from a third width adjacent the longitudinal connection region to a fourth width adjacent an inner valley of the at least one cell, the third width being greater than the fourth width.

2. The stent of claim 1, wherein the at least one cell includes a circumferential connection region at each circumferential end of the at least one cell, the at least one cell being symmetrical about an axis extending through the circumferential connection regions.

3. The stent of claim 2, wherein the at least one cell includes longitudinal connection regions at each longitudinal end of the at least one cell, the at least one cell being symmetrical about an axis extending through the connection longitudinal connection regions.

4. The stent of claim 2, wherein the first segments of the at least one cell are each dimensioned to continuously taper from the circumferential connection region to the respective first and second outer peaks of the at least one cell.

5. The stent of claim 4, wherein the second segment is dimensioned to continuously taper from the longitudinal connection region to the inner valley of the at least one cell.

6. The stent of claim 1, wherein the stent body is made of a shape-memory metal.

7. A stent comprising:
a stent body defining a longitudinal axis, the stent body including a plurality of structural members extending in an undulating pattern about a circumference of the stent body;
longitudinally adjacent structural members being connected to define a plurality of cells, each cell having a plurality of outer peaks and inner valleys coupled by segments that extend generally longitudinally between the outer peaks and inner valleys, at least some of the valleys of each cell being free from connection with adjacent valleys;
a longitudinal connection region connecting adjacent outer peaks of a pair of cells, the pair of cells being longitudinally spaced relative to the longitudinal axis of the stent body, wherein the pair of cells are symmetrical about a longitudinal axis defined through the longitudinal connection region;
each cell of the pair of cells including a first segment extending longitudinally from the longitudinal connection region to a first inner valley of the respective cell, each first segment having a width that tapers along the longitudinal axis from a first width adjacent the longitudinal connection region to a second width adjacent the respective first inner valleys of the pair of cells, the first width being greater than the second width; and
wherein each cell of the pair of cells includes a second segment extending longitudinally from the longitudinal connection region to a second inner valley of the respective cell, each second segment having a width that tapers longitudinally along the longitudinal axis from a third width adjacent the longitudinal connection region to a fourth width adjacent the second inner valley, the third width being greater than the fourth width.

8. The stent of claim 7, wherein a first cell of the pair of cells includes longitudinal connection regions at each longitudinal end of the first cell, the first cell being symmetrical about an axis extending through the longitudinal connection regions.

9. The stent of claim 8, wherein the first cell includes circumferential connection regions at each circumferential end of the first cell, the first cell being symmetrical about an axis extending through the circumferential connection regions.

10. The stent of claim 7, wherein the stent body is made of a shape-memory metal.

11. The stent of claim 7, wherein the pair of cells are arranged in alignment along the stent.

12. A stent comprising:
a stent body defining a longitudinal axis extending therethrough, the stent body including a plurality of structural members defining a plurality of cells, each of the plurality of the structural members extending in an undulating pattern about a circumference of the stent body;
each of the cells defined by the structural members including a plurality of outer peaks and inner valleys coupled by segments that extend generally longitudinally along the stent from the outer peaks to the inner valleys, each of the cells having at least some of the inner valleys being free from connection with adjacent inner valleys;
a first cell adjacent to a second cell, the first cell and the second cell being longitudinally spaced along the stent body, the first cell including an outer peak, the second cell including an outer peak, the outer peaks of the first and second cells being connected at a longitudinal connection region; and
at least a first segment of each of the first and second cells having a width that continuously tapers longitudinally along the stent from a first width adjacent to the longitudinal connection region to a second width adjacent to an inner valley of the respective first and second cells, the first width being different than the second width;
at least a second segment of each of the first and second cells having a width that continuously tapers longitudinally along the stent from a third width adjacent to the longitudinal connection region to a fourth width adjacent a second inner valley of the respective first and second cells, the third width being different then the fourth width; and
the first cell including longitudinal connection regions at each longitudinal end of the first cell, the first cell being symmetrical about an axis extending through the longitudinal connection regions.

13. The stent of claim 12, wherein the first cell includes circumferential connection regions at each circumferential end of the first cell, the first cell being symmetrical about an axis extending through the circumferential connection regions.

14. The stent of claim 12, wherein the stent body is made of a shape-memory metal.

15. A stent of comprising,
a stent body defining a longitudinal axis extending therethrough, the stent body including a plurality of structural members defining a plurality of cells, each of the plurality of the structural members extending in an undulating pattern about a circumference of the stent body;
each of the cells including a plurality of outer peaks and inner valleys coupled by segments that extend generally longitudinally along the stent from the outer peaks to the inner valleys, each of the cells having at least some of the inner valleys being free from connection with adjacent inner valleys;
a first cell adjacent to a second cell, the first cell and the second cell being longitudinally spaced along the stent body, the first cell including a first peak, the second cell including a second peak, the first peak and the second peak being adjacent to one another and connected along a length of the stent body at a longitudinal connection region;
the first cell including a first segment having a width that continuously tapers longitudinally along the stent from a first width adjacent to the longitudinal connection region to a second width adjacent to a first inner valley, the first width being different than the second width;
the first cell including a second segment having a width that continuously tapers longitudinally along the stent from a third width adjacent to the longitudinal connection region to a fourth width adjacent to a second inner valley; and
the first cell including longitudinal connection regions at each longitudinal end of the first cell, the first cell being symmetrical about an axis extending through the longitudinal connection regions.

* * * * *